United States Patent [19]
Santus et al.

[11] Patent Number: 5,503,843
[45] Date of Patent: Apr. 2, 1996

[54] TRANSDERMAL DELIVERY OF ALPHA ADRENOCEPTOR BLOCKING AGENTS

[75] Inventors: Giancarlo Santus, Milan, Italy; Aeri Kim, Mountain View, Calif.; Michael L. Francoeur, Los Altos, Calif.; Ulrike Bremer, Menlo Park, Calif.

[73] Assignee: Flora Inc., Menlo Park, Calif.

[21] Appl. No.: 231,413

[22] Filed: Apr. 22, 1994

[51] Int. Cl.⁶ .................................................. A61F 13/00
[52] U.S. Cl. .......................... 424/448; 424/449; 514/252
[58] Field of Search ...................................... 424/448, 449

[56] References Cited

U.S. PATENT DOCUMENTS

| | | | |
|---|---|---|---|
| 4,645,502 | 2/1987 | Gale | 604/896 |
| 4,661,491 | 4/1987 | Regnier | 514/260 |
| 4,668,506 | 5/1987 | Bawa | 424/429 |
| 4,863,970 | 9/1989 | Patel | 514/784 |
| 5,041,437 | 8/1991 | Yoshida et al. | 514/268 |
| 5,403,847 | 4/1995 | Gluchowski et al. | |

FOREIGN PATENT DOCUMENTS

| | | |
|---|---|---|
| 0204597 | 12/1986 | European Pat. Off. |
| 0416804 | 3/1991 | European Pat. Off. |
| 0439320 | 7/1991 | European Pat. Off. |
| 0566288A1 | 10/1993 | European Pat. Off. |
| 0582502 | 2/1994 | European Pat. Off. |
| 89/10123 | 11/1989 | WIPO |
| 93/03697 | 3/1993 | WIPO |
| 93/17007 | 9/1993 | WIPO |
| 95/05169 | 2/1995 | WIPO ........................... A61K 31/35 |

OTHER PUBLICATIONS

Chem. Abst. 118, Abstract No. 27492, (1993), to Masao Mori.

Hansen, B. J. et al. (1993) *Eru. Urol.* 24(suppl 1):41–49.

*Primary Examiner*—D. Gabrielle Phelan
*Attorney, Agent, or Firm*—Darby & Darby

[57] ABSTRACT

The subject invention provides a transdermal patch for the delivery of Compound IV having the formula:

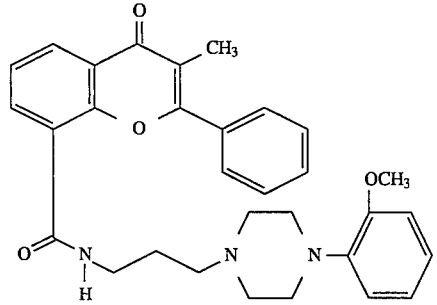

to the skin of a patient. The patch comprises a backing layer, a drug depot comprising Compound IV and a permeation enhancer composition.

20 Claims, 2 Drawing Sheets

TRANSDERMAL DELIVERY OF ALPHA ADRENOCEPTOR BLOCKING AGENTS

The present invention relates to the transdermal administration of alpha-adrenoceptor blocking compounds, and more particularly, the transdermal administration of Rec 15/2739.

BACKGROUND OF THE INVENTION

Adrenergic nerve fibers comprise the majority of the postganglionic nerve fibers, having norepinephrine as the primary neurotransmitter. Autonomic nerve impulses induce adrenergic responses in many bodily organs. The responses are varied, including blood vessel constriction, constriction of the stomach, intestinal, and genito-urinary sphincters, bronchial muscle relaxation and increased heart rate.

Agents that block responses to adrenergic nerve activity through interaction with alpha-adrenoceptors are referred to as alpha adrenergic blocking agents. The blocking agents selectively inhibit responses to adrenergic sympathetic nerve activity and to epinephrine and other sympathomimetic drugs. The response to sympathomimetic amines such as norepinephrine and isoproterenol was first used to categorize adrenergic receptors. The alpha receptors are potently affected by norepinephrine and very poorly affected by isoproterenol. On the other hand, the beta receptors are poorly affected by norepinephrine and potently affected by isoproterenol.

Alpha-adrenergic receptors (or alpha adrenoceptors), including the $alpha_1$ and $alpha_2$ subtypes, are found in many locations throughout the body. Thus, the alpha-adrenergic blocking agents (alpha-blockers) have been suggested to have, or have a variety of therapeutic uses, including the treatment of prostate and genito-urinary disorders such as benign prostatic hyperplasia (BPH); peripheral vascular disorders, including Raynaud's disease, acrocyanosis, frost bite, acute arterial occlusion, phlebitis, phlebothrombosis, diabetic gangrene, causalgia, shock and pheochromocytoma; hair loss; and hypertension, see Goodman and Gilman, *The Pharmacological Basis of Therapeutics* 7th Ed, 1985, MacMillan and Co., the contents of which are hereby incorporated by reference.

Although intravenous (i.v.) infusion of alpha blockers and other therapeutic agents is recognized as a superior mode of drug administration due to bypassing hepatic first pass metabolism and maintaining a constant and prolonged drug level in the body, such methods of drug administration require close medical supervision and may necessitate hospitalization. However, the transdermal administration of active agents offers many of the benefits of i.v. infusion, including direct entry of the drug into the systemic circulation and continual release of the drug. Transdermal delivery is also particularly advantageous for drugs having short half-lives, as maintenance of the required blood levels of these drugs required a higher frequency of bolus dose administration of the drug.

Transdermal delivery of active compounds also provides a non-invasive method for the controlled release and delivery of an active agent. This is advantageous as compared to non-controlled release methods, which may result in underdosing or overdosing of the drug. Other advantages of transdermal drug delivery may include reduction in dosing frequency, reduced fluctuation in circulating drug levels, increased patient compliance and convenience, and a more uniform effect. Transdermal delivery also avoids some of the disadvantages associated with oral drug delivery, such as gastrointestinal irritation. However, many drugs have been difficult to administer transdermally, due to the low skin flux or permeation rates of the drug and the amount of drug that must be delivered for therapeutic efficacy.

It would therefore be desirable to administer transdermally a therapeutically effective amount of an alpha adrenoceptor blocker.

SUMMARY OF THE INVENTION

The present invention provides compositions for the transdermal delivery of Rec 15/2739. The invention also provides methods of administering Rec 15/2739 to a patient in therapeutically effective amounts.

In one aspect, the invention provides a method of treating benign prostatic hyperplasia, the method comprising the transdermal administration of a therapeutically effective amount of Rec 15/2739.

In another aspect of the invention, there is provided a transdermal patch for the delivery of Rec 15/2739 to the skin of a patient, the patch comprising a backing layer, a drug depot including Rec 15/2739 and a permeation enhancer composition, and a means for affixing the patch to the skin of the patient. In some aspects, the permeation enhancer composition comprises a combination of permeation enhancers, including at least one plasticizer type enhancer, and may also include at least one solvent type enhancer.

In yet another aspect of the invention, there is provided a method for administering Rec 15/2739 to an individual in therapeutically effective amounts, the method comprising the transdermal delivery of Rec 15/2739 together with a permeation enhancer, so as to deliver at least about 0.01 mg of Rec 15/2739 per kg of body weight per day to the individual.

DESCRIPTION OF THE PREFERRED EMBODIMENTS

Unless defined otherwise, all technical and scientific terms used herein have the same meaning as commonly understood by one of ordinary skill in the art to which this invention pertains. Although any methods and materials similar or equivalent to those described herein can be used in the practice or testing of the present invention, the preferred methods and materials are described. For purposes of the present invention, the following terms are defined below.

The term "drug", "alpha blocker" or "active ingredient" as used herein, means "Rec 15/2739", including the free base, pharmaceutically acceptable salts of Rec 15/2739, hydrates, anhydrous form, and also includes prodrugs thereof.

The term "bioavailability" is the extent to which the drug reaches its site of action, or the extent to which the drug reaches a biological fluid (such as blood, and typically the general circulation) from which the drug has access to the site of action. For example, if a drug is metabolized in the liver or excreted in bile, some of the drug taken orally will be inactivated before it can reach the general circulation and exert its desired therapeutic effect. Bioavailability is defined in terms of a specific drug moiety, usually the active therapeutic entity, which may be the unchanged drug, or as with prodrugs, a metabolite.

The term "therapeutically effective level" as used herein refers to the minimal blood level of drug required to achieve a therapeutic effect.

The term "pharmaceutically acceptable" or "therapeutically acceptable" refers to a substance which does not interfere with the effectiveness or the biological activity of the active ingredients and which is not toxic to the host or patient.

The term "blockade" is used to indicate interference with a response system such that the final effect is prevented. Thus, the term "adrenergic blockade" indicates that the particular response system affected is that which normally involves the catecholamine neurohumoral transmitters, epinephrine (adrenaline) and norepinephrine (noradrenaline, levarterenol). The term "adrenergic" refers to any of the cellular apparatus concerned with the elaboration, storage, release, transmission, reception or action of these catecholamines or to their mimetics. Thus, the locus of an adrenergic blocking agent might be any one of these sites.

Figure 1:
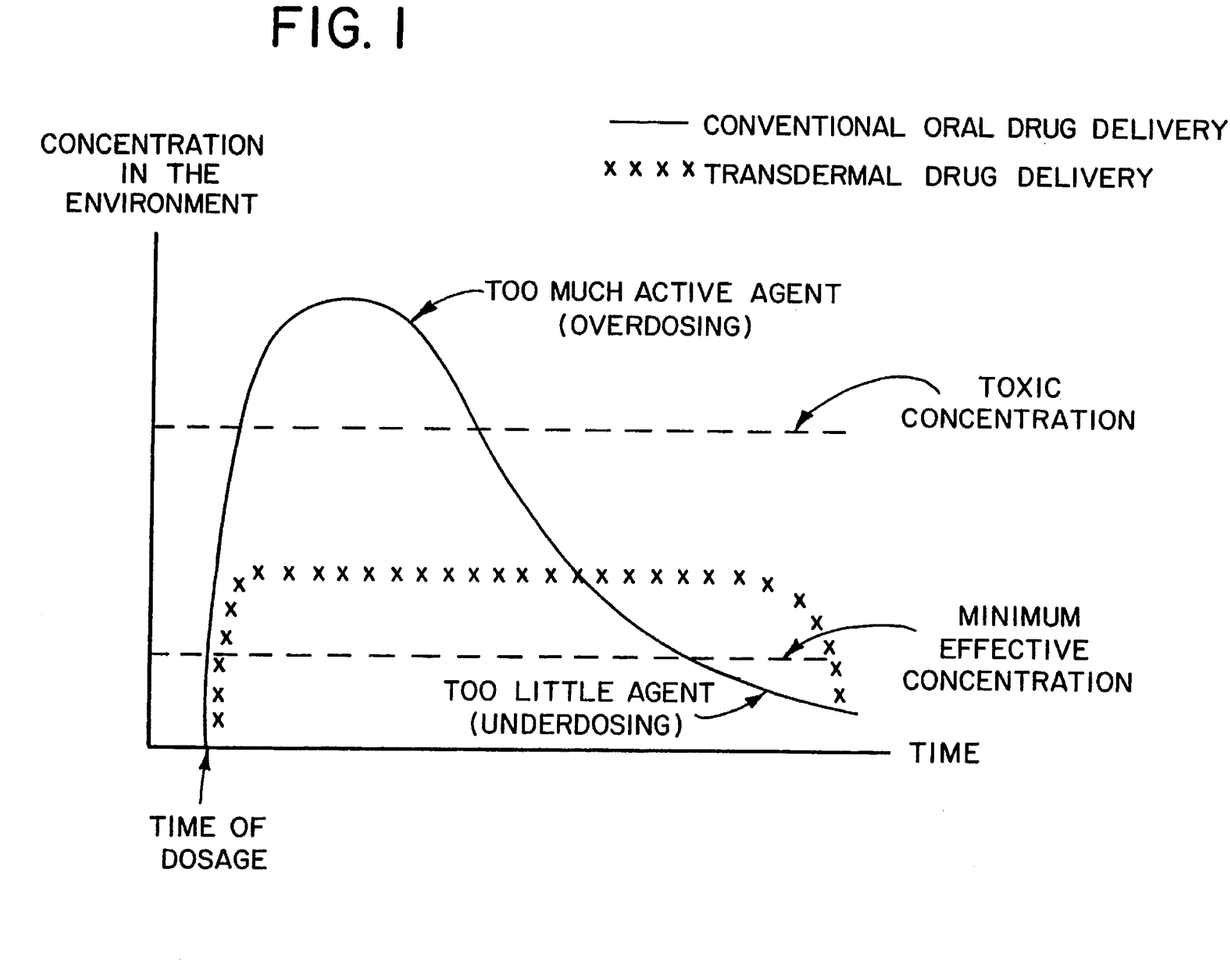
FIG. 1 shows the contrasting levels of drug in a system after conventional oral delivery and transdermal delivery.

When a drug is administered intravenously or orally, the initial level of drug in the blood rapidly rises to a maximum, which is generally much higher than the therapeutically effective level of the drug. For example, FIG. 1 shows that sometimes initial levels of drugs administered orally may reach toxic concentrations resulting in undesirable side-effects. This is known as "overdosing." After the maximum level in the blood is reached, the concentration then falls slowly as the drug is distributed, metabolized, excreted, or degraded. Eventually, the blood concentration of the drug falls below the therapeutically effective level (i.e., there is "underdosing"). At this point, the drug needs to be re-administered to achieve effectiveness. Maintaining the blood concentration of drug between the minimum therapeutically effective level and toxic levels is important. One way to achieve this is to administer lower drug doses to the patient more frequently. This, however, is an unacceptable alternative in most instances, due to problems with patient compliance.

Transdermal delivery of drugs offers a means of circumventing the problems of overdosing and underdosing that are associated with conventional drug delivery methods. The transdermal delivery of drugs can be designed so that the rate of delivery of the drug closely follows the rate of the clearance of the drug from the environment, thus keeping constant levels of drug in the blood, and reducing drug waste and overdosing problems. FIG. 1 displays the blood levels from transdermal as well as conventional oral delivery of drugs over a period of time, indicating the controlled release and delivery aspect of transdermal delivery, and the achievement of therapeutically effective levels of a drug for a prolonged duration.

In addition to the advantage of being able to control drug delivery rates, transdermal drug delivery also provides a comfortable, convenient and non-invasive method of administering drugs. Gastrointestinal irritation and other side-effects associated with oral drug delivery may be reduced or eliminated, and patient anxiety regarding invasive delivery methods, such as needles, is also eliminated.

Alpha adrenoceptors may be characterized as the $alpha_1$ or $alpha_2$ subtypes. The receptor subtypes are functionally categorized. Blockage of $alpha_1$ receptors inhibit vasoconstriction induced by endogenous catecholamines. Blockade of $alpha_1$ receptors also inhibits vasoconstriction and the increase in blood pressure produced by the administration of a sympathomimetic amine. On the other hand, activation of pre-synaptic $alpha_2$ receptors inhibits the release of norepinephrine from peripheral sympathetic nerve endings. Blockade of these $alpha_2$ receptors with selective antagonists can increase sympathetic outflow and potentiate the release of norepinephrine, leading to activation of $alpha_1$ and $beta_1$ receptors in the heart and peripheral vasculature, leading to an increase in blood pressure, as described in Goodman and Gilman, supra. In addition, post-synaptic and extra-synaptic receptors have been recently found, whose activation by catecholamines leads to an increase in blood pressure (E. Sylvester Vizi (1989) *Med. Res. Review* 6:431–449 and references cited therein). Therapeutic agents may be either selective or non-selective alpha blockers.

Non-selective alpha blockers include phenoxybenzamine, phentolamine, and ergot alkaloids. The non-selective alpha blockers may be used in the treatment of essential hypertension, renal hypertension, and peripheral vascular disorders in which there is an adrenergically-mediated vasospastic component such as Raynaud's disease, acrocyanosis, frost bite, acute arterial occlusion, pseudo obstruction of the bowel, phlebitis, phlebothrombosis, diabetic gangrene, causalgia, shock, pheochromocytoma, treatment of migraine, and as stimulants of post-partum uterine contractions.

Alpha blockers selective for the $alpha_1$ receptor subtype include alfuzosin, tamsulosin, prazosin, and terazosin. The use of these compounds to block the $alpha_1$ adrenergic impulses causes decreased vascular resistance and decreased blood pressure. Selective $alpha_1$ blockers may be used in the treatment of essential hypertension, renal hypertension, peripheral vascular disorders in which there is an adrenergically-mediated vasospastic component such as Raynaud's disease, acrocyanosis, frost bite, acute arterial occlusion, phlebitis, phlebothrombosis, congestive heart failure, diabetic gangrene, causalgia, shock and pheochromocytoma.

In addition, alpha-adrenergic blockers are effective in the treatment of the symptoms associated with BPH, Caine et al., *Br. J. Urol.* (1976) 138:979–983. The alpha blocker terazosin has also been suggested for the treatment of BPH, as reviewed in Hansen, B. J. and T. Hald, *Eur. Urol.* (1993) 24 (suppl): 41–49. BPH is a disease frequently found in older men, and may be present in up to 80% of males older than 60 years of age. Patients suffering from this condition experience obstructive urinary symptoms including hesitancy and difficulty in initiation of urination, in interruption and quality of flow, weakening of the urinary stream, and sensations of incomplete emptying. In addition, patients experience irritative urinary symptoms, such as nocturia, increased frequency, and urgency. Although oral doses of terazosin have been suggested to be effective in the treatment of BPH, concerns remain over potential high dose side effects such as postural hypotension and loss of consciousness, see for example, Goodman and Gilman, *The Pharmacological Basis of Therapeutics*, supra. Thus, the development of a convenient, non-invasive drug administration system for compounds effective in the treatment of BPH is highly desirable. The preferred system for administration of these compounds according to the present invention is a transdermal patch.

5-[2-[[2-(o-Ethoxyphenoxy)-ethyl]amino]propyl]-2-methoxybenzenesulfonamide (also known as amusulosin, amsulosin, YM12617, YM617 or tamsulosin) is a selective alpha$_1$ receptor blocker. The structure of tamsulosin is shown in Formula I below.

FORMULA I

Tamsulosin reduces the contraction of the rabbit and guinea pig prostrate, urethra, and vesical triangle, and of the human urethra and vesical triangle, Honda et al., Alpha-1 Adrenoceptor antagonist effect of the optical isomers of YM12617 in rabbit lower urinary tract and prostate, J. Clin. Pharmacol. Exptl. Therapeutics (1986) 239(2): 512–516, and Honda et al. Further studies on (±) -YM12617, a potent and selective $\alpha_1$-adrenoceptor antagonist and its individual optical enantiomers, Arch. Pharmacol. (1987) 336: 295–302. Thus, tamsulosin is expected to have activity in diseases where bladder, prostate, or vasosphincter musculature is compromised, for example, erectile dysfunction, BPH, dysuria or urinary incontinence.

Alfuzosin, N-[3-[(4-Amino-6,7dimethoxy-2-quinazolinyl) methylamino]propyl]tetrahydro-2-furancarboxamide, is a quinazoline derivative and is a selective alpha$_1$ blocker with antihypertensive activity, and direct peripheral vasodilating properties. Radioligand binding and phosphate accumulation studies demonstrate that alfuzosin possesses similar affinity for both alpha$_1$A and alpha$_1$B adrenoceptors and lacks any relevant selectivity for alpha$_1$ subtypes, Michel, M. C. et al., Naunyn-Schmiedeberg's Arch. Pharmacol. (1993) 348: 385–395. The structure of alfuzosin is shown in Formula II.

FORMULA II

Alfuzosin also shows activity in altering the phenylephrine induced contractions on preparations of smooth muscle originating from the trigone muscle at the base of the bladder. Thus, alfuzosin is expected to have activity in diseases where bladder, prostate, or vasosphincter musculature is compromised, for example, erectile dysfunction, BPH and dysuria or urinary incontinence.

Alfuzosin is typically administered as the racemic mixture. In vitro, the R and S enantiomers are equally potent in antagonizing phenylephrine, a sympathomimetic agent induced contraction in both rabbit trigone and urethral ring tissues, Wilde et al., Drugs (1993) 45(3) 410–429.

Typical dosages of alfuzosin are in the range of about 4–15 mg of the racemic mixture per day. The mean oral bioavailability of alfuzosin is 64%, Wilde et al., supra, and the plasma half life of the drug is reported as between 4–9 hours, thus necessitating a twice or three times daily oral dosage regimen to maintain a constant therapeutically effective plasma blood level, S. Lieto di Priolo et al., Dose-Titration Study of Alfuzosin, a New Alpha$_1$-Adrenoceptor Blocker in Essential Hypertension, Eur. J. Clin Pharmacol (1988) 35: 25–30.

Terazosin [1-(4-amino-6,7-dimethoxy-2-quinazonlinyl)- 4-[tetrahydro- 2-furanyl)carbonyl]piperazine] is a selective alpha$_1$ blocker with anti-hypertensive activity, as described in Titmarsh, S., et al. (1987) Drugs 33:461–477. The structure of terazosin is shown in the Merck Index, 11th Edition, the contents of which are incorporated by reference, and in Formula III.

FORMULA III

8(3-[4-(2-methoxyphenyl)-1-piperazinyl]-propylcarbamoyl)-3 -methyl-4-oxo-2-phenyl-4H-1-benzopyran and its salts, hereinafter "Rec 15/2739", is an anti-adrenergic compound, as described in U.S. patent application Ser. No. 07/888,775 and PCT International Publication No. WO93/17007, the contents of which are hereby incorporated by reference. The structure of Rec 15/2739 is shown in Formula IV.

FORMULA IV

Rec 15/2739 has affinity and selectivity for the alpha$_1$ adrenergic receptors, and exhibits high selectivity for the mammalian lower urinary tract. That is, the compound is substantially more active in antagonizing urethral contractions than in lowering blood pressure. On the other hand, alpha$_1$ antagonists such as prazosin do not exhibit such selectivity, and in fact cause hypotension as a most common side effect. Thus, the active ingredient of the invention is useful for the treatment of hypertension and micturition troubles associated with obstructive disorders of the lower urinary tract, including benign prostatic hyperplasia. The active ingredient may also find use as an anti-hypertensive agent. In these latter applications, decreased selectivity requires an increased dosage of drug, but the low toxicity of the drug permits high doses. The compounds demonstrate antagonistic effects against contractions of rat bladder strip induced by potassium chloride, and described in PCT Publication No. WO/93,17007, the contents of which are hereby incorporated by reference. This effect may be attributed to a calcium antagonistic activity, and renders the active ingredient useful as antispasmodics of the lower urinary tract, and thus useful in the treatment of urinary incontinence, urge syndrome, and the like.

In one embodiment of the invention the alpha blockers are present as mesylate ($CH_3SO_3^-$) salts. Many salt forms of active compounds, for example inorganic, sulfonic and carboxylic acid salts tend to increase the melting point of the drug over the neutral free base form, thereby improving the stability and processing of basic drugs. In addition, the choice of salt form may alter the solubility of the compound. Changing from a neutral form of a drug to a salt form affects the pH of the resulting solution, and a number of physical parameters, including melting point, molecular weight, stability, hygroscopicity and solubility.

However, the solubility improvement largely depends on the choice of solvent, any specific common ion interaction and the size and polarity of the counterion. Often, salts prepared from strong acids are freely soluble in water. Strong acids are those with a $pK_a$ of less than 2, and are completely ionized in solution. According to the present invention, salts of strong alkane- or arenesulfonic acids may be used in pharmaceutical compositions to provide counterions for the manipulation of the performance of basic salt drugs. Suitable alkane- or arenesulfonic acid anions include sulfate, tosylate (para-toluenesulfonate), mesylate (methanesulfonate), napsylate (1-napthalene-2-sulfonate), besylate (benzene sulfonate) and maleate. Table 1 provides the melting point and molecular weight of the free base, hydrochloride, and mesylate salt forms of select alpha blockers of the present invention.

TABLE 1

| DRUG | MW | MP (°C.) | ORAL DOSE mg/day | pKa |
|---|---|---|---|---|
| Prazosin free base | 383.4 | 279 | 2–20 (hypertension) | 6.5 |
| hydrochloride | 419.9 | 264 | | |
| mesylate | 479.8 | | | |
| Terazosin free base | 387.4 | 278.5 | 1–20 (hypertension) | 7.1 |
| hydrochloride | 423.9 | 272 | | |
| mesylate | 484 | 257 | | |
| Phentolamine free base | 281.4 | 174.5 | 200–300 (hypertension) | |
| hydrochloride | 317.8 | 240 | | |
| mesylate | 377.5 | 179 | | |
| Phenoxybenzamine free base | 303.8 | 39 | 20–120 (hypertension) | |
| hydrochloride | 340.3 | | 10–20 (BPH) | |
| mesylate | 400.2 | | | |
| Alfuzosin free base | 389.4 | 178–182 | 7.5–10 (BPH) | 8.13 |
| hydrochloride | 425.9 | 229 | | |
| mesylate | 485 | 214 | | |
| Rec 15/2739 free base | 512 | 134 | 2–20 | 7.0 |
| hydrochloride.H$_2$O | 566.1 | 152.5 | | |
| 2 HCl | 593.5 | | | |
| mesylate | 607.7 | 166 | | |
| Tamsulosin free base | 408.6 | 130 | 0.1–0.4 | |
| hydrochloride | 445 | 229 | | |
| mesylate.H$_2$O | 523 | 93.5 | | |

Table 2 provides the solubility of the free base forms of the alpha blocker Rec 15/2739 in various vehicles. Solubility of free base is indicated as μg per ml of medium. PBS indicates phosphate buffered saline (20 mM phosphate and 0.9% NaCl).

TABLE 2

| Medium | Solubility |
|---|---|
| saline | 1.5 |
| PBS pH 6.7 | 5.2 |
| PBS pH 5.2 | 68 |

For adequate skin penetration of most drugs, a chemical permeation enhancer is necessary. As used herein, the term "enhancer" is meant to encompass any enhancer or combination of enhancers that increases the flux of a substance across a mammalian stratum corneum. The enhancer that results in the highest skin flux is often specific to a particular drug and what works for one drug may not work for another. Furthermore, the precise concentration of enhancer and the particular combination of enhancers must be tailored to each drug to achieve the maximum skin flux. There are numerous possible permeation enhancers that can be used and they are typically categorized into two groups, solvent-type enhancers and plasticizing-type enhancers.

Plasticizer-type enhancers refers to fatty acids, fatty acid esters, fatty alcohols and similar hydrophobic compounds that are capable of increasing the permeability of drugs to the stratum corneum. Without limiting the scope of the present invention, the following is proposed as the mechanism of action of the plasticizer-type enhancers. It is believed that the function of the plasticizer-type enhancers is to migrate into the upper stratum corneum layers of the skin and disrupt the lipids which occupy the extracellular spaces of the stratum corneum. The stratum corneum layer, although only 25–50 microns thick, is the principal barrier to transdermal permeation. The plasticizer-type enhancers that migrate into the skin serve to increase the mobility and diffusion of the drug into the skin.

Plasticizer-type enhancers generally will have a molecular weight of greater than 150 but less than 1000. In addition, the plasticizer-type enhancers should also be relatively water insoluble or they will leach into the subcutaneous tissue layers below the stratum corneum. Thus, plasticizer-type enhancers with water solubility of less than 0.5 wt % are preferred, and more preferably 0.2 wt % or less.

Enhancers may also be classified according to their Hildebrand solubility parameters. The Hildebrand solubility parameter measures the cohesive forces and sum of all intermolecular attractive forces related to the extent of mutual solubility of many chemical species. See, e.g. the CRC Handbook of Solubility Parameters and other Cohesion Parameters, CRC Press, Inc., Boca Raton, Fla. (1985). Relative hydrophilicity increases with the value of the Hildebrand solubility parameter ($\sigma$). For example, the skin has a $\sigma$ value of 10, while water has a G value of 23.4. This implies that enhancers with solubility parameters of <10 will intervene with the lipid component of the skin, but those with solubility parameters of >10 will selectively partition into the polar components of the skin. Generally, plasticizer type enhancers have a $\sigma$ value of between about 5 and 10.

A preferred group of plasticizer-type enhancers includes lower alkyl and alkoxy esters of pharmaceutically acceptable fatty acids, fatty acid esters, fatty alcohols, and similar hydrophobic compounds. As used herein, the term 'lower alkyl and lower alkoxy' refers to alkyl and alkoxy groups having up to and including 7 carbon atoms and preferably, up to and including 4 carbon atoms. Some examples of alkyl groups include methyl, ethyl, propyl, isopropyl, n-butyl, tertiary butyl, pentyl, isopentyl, neopentyl, hexyl, isohexyl and heptyl. Some examples of alkoxy groups include the oxides corresponding to the above alkyl groups. Examples of suitable fatty acid esters include saturated or unsaturated fatty acid esters, including isopropyl myristate, isopropyl palmitate, and the methyl and ethyl esters of oleic and lauric acid. Suitable fatty alcohols include stearyl alcohol and oleyl alcohol. Examples of suitable fatty acids include saturated and unsaturated fatty acids, including oleic acid, lauric acid, myristic acid, palmitic acid, stearic acid, linoleic acid, and palmitoleic acid. In addition, many other compounds can also serve as plasticizer-type enhancers, such as diethyl hexyl phthalate, octyldocecyl myristate, isostearyl isostearate, caprylic/capric triglycerides including polyethylene glycol esters of caprylic/capric acids, propylene glycol laurate (Lauroglycol), Miglyol (propylene glycol diester caproic, caprylic, capric, lauric acid), Lexol PG-865 (propylene glycol diester decanoic, octanoic acid), propylene glycol myristate (mirpyl), corn oil polyethylene glycol-6 esters (Labrafil M2124CS), polyethylene glycol-8 caprylic capric glycerides (Labrasol), caprylic/capric triglycerides (Labrafac Lipophile WL 1349), caprylic/capric triglyceride polyethylene glycol-4 esters (Labrafac Hydro WL1219 available from Gattefosse, Westwood N.J.), glyceryl oleate, hexamethyldisiloxane, m\dimethicone, cyclomethicone, squalene, mineral oil, macrocyclic ketones/lactones, plant extracts such as Chrodarom Calendula O or Chrodarom Chamomile O, and various oils including wintergreen, jojoba oil, or eucalyptol (cineole). A preferred plasticizer-type enhancer for use with the mesylate salt of Rec 15/2739 include caprylic/capric acids triglyceride PEG-4 esters, available as Labrafac Hydro WL 1219, (Gattefosse, Westwood, N.J.) which contains a mixture of saturated polyglycolyzed glycerides consisting of glycerides and polyethylene glycol esters of caprylic and capric acids. One of skill in the art would appreciate that the plasticizer-type enhancers may be used alone or in combination. A particularly preferred enhancer combination including the caprylic/capric triglycerides for use with the mesylate salt of Rec 15/2739 is an enhancer vehicle consisting essentially of ethanol:caprylic/capric triglycerides polyethylene glycol-4 ester:propylene glycol:isopropyl myristate in a 1:1:1:1 ratio.

As used herein, "solvent-type enhancer" generally refers to relatively hydrophilic compounds having molecular weights of less than about 200 that are capable of increasing the permeability of drugs to the stratum corneum. Solvent-type enhancers typically exhibit solubility parameters between about 10 and 24, and preferably between about 10 and 18. Solvent-type enhancers are often better enhancers because they generally provide higher flux rates for a given permeant than plasticizer-type enhancers. Typically, the solvent type enhancers will comprise a pharmaceutically-acceptable lower alkyl alcohol, aryl alcohol, or polyol, for example, ethanol, propanol, butanol, benzyl alcohol, glycerin, or propylene glycol. In some embodiments, the solvent-type enhancer is a 2-pyrrolidone or alkyl derivative thereof, such as N-methyl-2-pyrrolidone, 3-hydroxy-N-methyl-2-pyrrolidone, and pyroglutamic acid esters.

Other embodiments may employ an alkyl ether, such as ethylene, polyethylene or propylene glycol ether, as the solvent type enhancer. Preferred examples of ethylene glycol ethers include, but are not limited to, ethylene glycol monoalkyl ethers, such as ethylene glycol monomethyl ether (also known as methyl cellosolve), ethylene glycol dialkyl ethers, such as ethylene glycol dimethyl ether (also known as dimethyl cellosolve), and ethylene glycol monoalkyl ether esters, such as ethylene glycol monoethyl ether acetate (also known as cellosolve acetate). Preferred examples of polyethylene glycol ethers include, but are not limited to, diethylene glycol monoalkyl ethers, such as diethylene glycol monobutyl ether (also known as butyl ethyl Cellosolve or butyl carbitol), diethylene glycol dialkyl ethers; and diethylene glycol monoalkyl ether esters, such as diethylene glycol monoethyl ether acetate (also known as Carbitol acetate), and transcutol (diethylene glycol monoethyl ether).

Preferred solvent type enhancers have a molecular weight of less than about 150. They are also relatively hydrophilic, generally being greater than 2 wt % soluble in water, and are preferably greater than 10 wt % soluble in water. Most preferred solvent type enhancers are completely water miscible. One of skill in the art would appreciate that the solvent type enhancers may be used alone or in combination.

While solvent type enhancers may be useful in delivering large amounts of therapeutic agents through the skin, when used alone, larger amounts of the solvent enhancer must often be applied continuously to achieve a prolonged therapeutic effect, to the extent that they themselves are permeable through the skin. As such, skin irritation may occur.

However, when one or more plasticizer-type enhancers is used in combination with one or more solvent-type enhancers, drugs can be delivered through the stratum corneum at therapeutically effective levels. Such an enhancer mixture achieves high delivery rates of the drug with relatively dilute solutions of the solvent-type enhancer. This tends to eliminate the irritation that occurs when solvent-type enhancers are used alone at high concentrations.

When used with plasticizer-type enhancers, the function of the solvent type enhancer is to rapidly diffuse into the stratum corneum layer of the skin, making it possible for the larger, less mobile plasticizer type enhancers to enter the stratum corneum layer. The small size and hydrophilic nature of the solvent type enhancers makes them very effective in this role.

Patch Configurations

The design of the transdermal patch for use according to the invention involves several factors including the permeability of drug to the skin, the dose of the drug required for the desired therapeutic application, the enhancers used to promote delivery of the drug, and the flux rate of drug and enhancer formulations required to achieve a therapeutic effect. Each active compound has unique physical and chemical properties that influence the design of the patch for effective delivery of the active compound to the patient. Various patch designs may be used in accordance with the present invention, as exemplified in FIGS. 2 through 4.

For delivery of the alpha blockers of the present invention, the optimal patch configuration and enhancer combination and concentration is assessed experimentally in vitro using two common methods, skin permeation testing and dissolution release tests. In the dissolution release test, the transdermal device is placed in a volume of receiving fluid sufficient to maintain sink conditions, which is stirred continuously and is maintained at a constant temperature. The cumulative amount of drug or enhancer released into the receiving medium is measured as a function of time. This test allows for confirmation of drug release from the transdermal device as well as a gross discrimination in drug release as a function of transdermal device components and formulation composition. However, the majority of screening is provided via in vitro skin tests. These tests provide a more realistic picture of the device performance in vivo. In these tests, the test solution or the transdermal device is placed in contact with the skin which is in contact with a receiving phase, usually saline. The amount of drug permeating throughout the skin is determined by monitoring the drug concentration in the receiving phase as a function of time. See, for example, Ritschel and Barkhaus (1987) *Meth. and Find. Exptl. Clin. Pharmacol.* 9: 673–676. These tests are more costly and time consuming than dissolution release tests yet better reflect the actual in vivo performance of the transdermal device. Enhancer selection and composition may be optimized by empirical testing.

Simple Adhesive Matrix Patches

Figure 2:
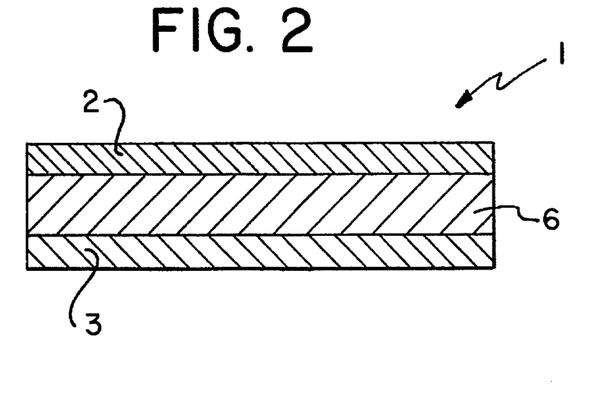
FIG. 2 shows a cross section of a simple adhesive patch having an impermeable tacking layer, a drug containing adhesive layer, and a release liner.

In one embodiment of the invention, the transdermal patch for the delivery of Rec 15/2739 is a simple adhesive patch, as shown in FIG. 2. In FIG. 2, the patch 1 comprises an impermeable backing layer 2, a release liner 3, and a drug/adhesive containing matrix 6.

The impermeable backing layer 2 defines the top of the drug delivery device, i.e., the side furthest away from the skin when the device is in use. The backing forms an occlusive layer that prevents the loss of drug and/or enhancers to the environment and protects the patch from contamination from the environment. The backing layer may be opaque so as to protect the drug from light.

The backing layer can be made from standard commercially available films for medical use, such as those supplied by 3M Corporation, St. Paul, Minn.; Dow Chemical, Midland, Mich.; or AF Packaging, Winston-Salem, N.C. Suitable materials which can be used to form the backing layer include films or sheets of polyolefin, polyester, polyurethane, polyvinyl alcohol, polyvinylidene, polyamide, ethylene-vinylacetate copolymer, ethylene-ethylacrylate copolymer, and the like, metal-vapor deposited films or sheets thereof, rubber sheets or films, expanded synthetic resin sheets or films, unwoven fabrics, fabrics, knitted fabrics, paper, and foils. These materials can be used individually or as laminates. These films can be pigmented or metalized.

Preferred backing layers include Scotchpak® 1006 and 1009, skin-colored aluminized polyester films of approximately 70–80 μm in thickness, and 3M-1012, a transparent polyester film laminate, all of which are available from 3M Corporation.

In some aspects of the invention, the patch may include a peel strip or release liner 3 to cover the surface of the pressure-sensitive adhesive during storage, and prevent evaporative loss of the drug or enhancer(s). The release liner may be formed with dimples for decreasing contacting surface with the adhesive layer, and it may also be formed with a pull-tab for making it easier for removing it from the device.

The peel strip may be made from any impermeable film, such as is specified for the backing layer. Additionally it may be made from metal foil, Mylar® polyethylene terephthalate, or any material normally used for this purpose in the art that is compatible with the drug and the chosen adhesive. Examples of suitable compositions for the release liner include siliconized polyester, poly (1,1-dihydroperfluoroctylmethacrylate), fumed silica in silicone rubber, end-capped siliconized polyethylene terephthalate, polytetrafluoroethylene, cellophane, a film of polyvinyl chloride having titanium dioxide dispersed therein, and the like. Preferred release liners include a silicon coated Release Technology 381B and fluoropolymer coated polyester films, such as 3M Scotchpak® 1022 film.

In the simple adhesive matrix patch of FIG. 2, the drug depot layer is comprised of the drug and an adhesive, the layer attaching directly to the skin of the patient after the peel strip or release liner is removed. In the preferred embodiments of the invention, the drug depot layer also comprises one or more enhancers.

Generally, the selection of the adhesive is important to the proper functioning of the transdermal delivery device. This is particularly true if a plasticizer-type enhancer is placed in the adhesive layer. Specifically, the adhesive layer must retain its functioning properties in the presence of the plasticizer-type and solvent-type enhancers, as well as upon exposure to the alpha blocker. However, often enhancers or other formulation ingredients can compromise the physicochemical and functional properties of an adhesive. Significant loss of cohesive strength can result in undesirable effects such as an increase in tack, cold flow beyond the edge of the patch, transfer of the adhesive to the protective release liner during removal, or adhesive residue left on the skin following removal of the patch. Alternatively, in some cases, the patch loses adhesion altogether and falls off. The loss of tack and other adhesion properties generally dictates and limits the amount and type of enhancers that can be loaded into the adhesive matrix type patches. In addition, as the structural integrity of the dosage unit is lost, the delivery rate of the drug is diminished and/or becomes variable and unstable.

For example, silicon adhesives are commonly used in transdermal delivery devices; however, they are capable of a maximum compatible loading of only about 1% isopropyl myristate. See Pfister et al. (1990) *Pharm. Tech. Int.* 55–59, Pfister and Hsieh (1991) *Pharm. Tech. Int.* 3:38–32, and Pfister and Hsieh (1991) *Pharm. Tech. Int.* 3:32–36. Since the adhesive layer of the devices described herein contain a high level of plasticizer-type enhancer, typically from about 5 to about 50 wt % of a plasticizer-type enhancer, based on the adhesive layer, and preferably from about 10 to about 40 wt %, and more preferably from about 25 to about 35 wt %, the proper selection of the adhesive is important for the performance of these transdermal delivery devices.

Preferably, the adhesives employed in the transdermal delivery systems described herein will have shear values greater than 2, with the higher values being preferred; plasticity values between about 1 and 4, and preferably greater than 1.5, with the higher values being preferred; tack values between about 50 and 1000, with the lower values being preferred; a dynamic loss modulus between about $10^{-5}$ and $10^{-7}$ at frequencies of $10^{-2}$ rad/sec and between $10^{-5}$ and $10^{-7}$ at frequencies of $10^{2}$ rad/sec; and a dynamic storage modulus between about $10^{-5}$ and $10^{-7}$ at frequencies of $10^{-2}$ rad/sec and between $10^{-5}$ and $10^{-7}$ at frequencies of $10^{2}$ rad/sec. See Chang (1991) *J. Adhesion* 34:189–200 and European Patent Publication No. 524,776. Cross-linked acrylate-based adhesives, such as those available from Avery Chemical Division, Mill Hall, Pa. and National Starch and Chemical Company, Bridgewater, N.J., are able to withstand relatively high loading of enhancers, both solvent-type and plasticizer-type, while still maintaining these performance parameters. These adhesives generally contain about 1 to about 5 wt % of acrylic acid, about 5 to about 20 wt % of a $C_4$ to a $C_{12}$ alkyl acrylate or alkyl methacrylate. The adhesives also can contain about 0.1 to about 5 wt % of a cross-linking monomer.

Preferred adhesive for delivery of Rec 15/2739 of the present invention are acrylate-based adhesives. Acrylate-based adhesives for use according to the present invention include Avery 2533 and Avery-460HPX adhesives (available from Avery Chemical Division (U.S.), Mill Hall, Pa.), Durotak® 87-2516, 87-2852, and 87-2287 (available from National Starch, Bridgewater, N.J.), and Monsanto's Gelva GE 1753. The acrylate adhesives Avery 2533 and Avery 460-HPX are similar acrylate adhesives with varying levels of cross linking. The Durotak® 87-2516, 87-2852 and 87-2287 are acrylic solution pressure sensitive adhesives, with the 2516 and 2852 being cross-linking and the 2287 being non-crosslinking.

Monolithic Matrix Patches

Figure 3:
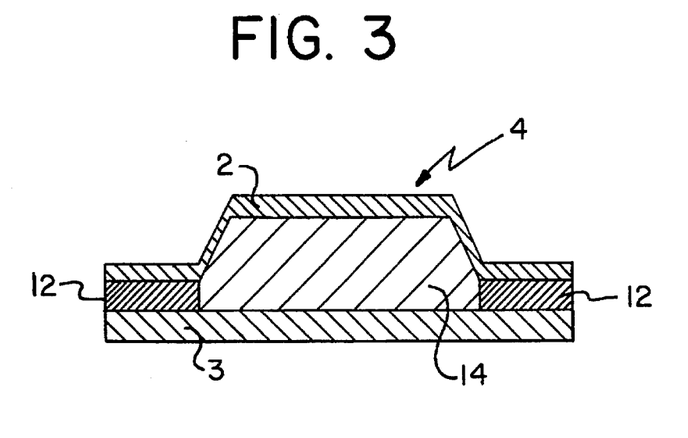
FIG. 3 shows a cross section of a monolithic matrix transdermal patch having an impermeable backing layer, a drug depot comprising a polymer matrix in which drug is dispersed, a peripheral adhesive layer, a release liner. The patch may also contain a porous membrane.

FIG. 3 shows a monolithic matrix patch, an alternative embodiment of the transdermal patch of the invention. In FIG. 3, the patch 4 comprises an impermeable backing layer 2, a release liner 3, a monolithic matrix layer 14 comprising a polymer matrix in which drug is dispersed, and a peripheral adhesive layer 12. In some embodiments, the patch may also include an optional porous membrane layer. In yet other embodiments, the patch may have an adhesive layer that is co-extensive with the skin facing surface of the patch. The monolithic matrix layer 14 comprises the drug, and one or more enhancers dispersed in a polymeric matrix.

The monolithic matrix layer may also comprise additional components such as diluents, stabilizers, vehicles, biocides, antioxidants, anti-irritants and the like. A preferred embodiment of the monolithic matrix patch is a monolithic matrix patch with a peripheral adhesive annular ring and a drug depot having a hydrogel matrix or a foam matrix.

Reservoir Type Patches

Figure 4:
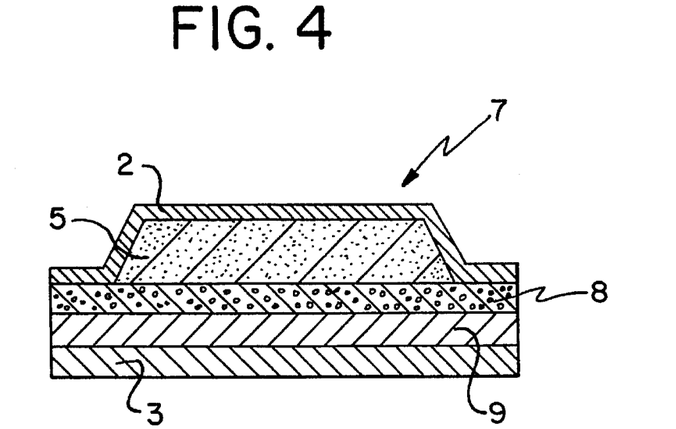
FIG. 4 shows a cross section of a reservoir type transdermal patch having an impermeable backing, a drug depot, a porous membrane, an adhesive layer, and a release liner. The backing layer and the membrane are sealed at their peripheral edges, thus defining a drug depot.

A further embodiment of the invention is the reservoir type patch which allows a higher loading level of active material, and usually, a higher loading level of enhancer. An example of the reservoir type patch is shown in FIG. 4. The patch 7 is comprised of an impermeable backing layer 2 which is sealed at its periphery to an inert membrane 8, thereby defining between these two layers a drug depot 5. An adhesive layer 9 is affixed to the skin facing side of the patch. The patch also comprises a release liner 3. The drug depot contains the drug, and optionally one or more enhancers or gelling components. Thus, in the reservoir type patches, a membrane separates the drug reservoir from the adhesive layer. In some embodiments the membrane is a non-rate controlling membrane. According to the present invention, a non-rate controlling membrane is one in which the rate of permeation of the enhancer(s) and drug through the membrane is greater than their permeation rate through the skin or any other portion of the device (typically two to five times greater or more). Thus, a non-rate controlling membrane is extremely permeable to the enhancer(s) and the drug contained in the reservoir.

In other embodiments, the membrane may be a rate-controlling membrane. As used herein, a rate-controlling membrane is one in which the rate of permeation of the enhancer(s) and the drug through the membrane is less than or equal to their permeation rate through the skin or any other portion of the device. Rate-controlling membranes are described, for example, in U.S. Pat. Nos. 4,460,372 and 4,379,454.

The membrane may comprise a microporous or porous material. Microporous membranes have a distinct pore structure with pores ranging in diameter from approximately 0.08 to 0.5 microns, preferably from about 0.1 and 0.4 microns, and more preferably from about 0.2 and 0.4 microns. Examples of suitable microporous membranes include polyethylene and polypropylene films, nylon, and nitrocellulose film. A preferred membrane material is Cotran® 9710, which is a polyethylene membrane, 50 μm in thickness, with a void volume of greater than 10%, available from 3M Corporation. Other embodiments of the present invention will utilize other microporous polyethylene membranes, such as Celgard K-256, available from Hoechst-Celanese, Charlotte, N.C. Porous membranes have pores greater than about 3 microns in diameter. Such materials are available as woven and non-woven fabrics, such as non-woven polyester #9770 from Dexter Corp. (Windsor Locks, Conn.). These materials can also be fabricated from nylon, polyethylene, polyolefins and the like.

In the reservoir type patches, the membrane and the backing layer are sealed at their peripheral edges to form the drug reservoir. This seal should be substantially fluid-tight to prevent drug leakage from the reservoir through the seal between the backing layer and the membrane. As used herein, the term "peripheral edges" of the membrane and backing layers refer to the areas that are sealed together to define the drug reservoir. Therefore, extraneous membrane and backing layer material may extend outwardly from the drug reservoir and peripheral edge.

The drug reservoir contains a solution, suspension, or gel of the drug and the permeation enhancers, as well as diluents, such as water, and vehicles or other additives. The drug can be dispersed in the solution, suspension, or gel in either a dissolved or undissolved state.

A gelling agent may be incorporated into the reservoir or monolithic matrix to increase the viscosity and rheological characteristics of the drug and enhancers. The agent also serves to prevent settling of the dispersed drug during storage. Typically, a viscosity range of about 100 to 100,000 centipoise for the combination of materials forming the reservoir is necessary in order to produce the drug delivery device using form-filling technology, as described in greater detail below.

The gelling agent comprises a pharmaceutically-acceptable material that is capable of increasing viscosity of the reservoir solution. Typically, the drug delivery devices described herein will employ cellulosic materials as the gelling agent. Examples of suitable cellulosic materials include cellulose, cellulose derivatives, alkylcellulose, hydroxy-(lower alkyl) cellulose derivatives where the alkyl group contains one to six carbons, carboxyalkylcellulose and the like. Other gelling agents include PVP, CMC, Klucel, alginates, kaolinate, bentonite, or montmorillonite, other clay fillers, stearates, silicon dioxide particles, carboxy polymethylene, ethylene maleic anhydride, polyacrylamide, and poly (methyl vinyl ether maleic anhydride.)

A preferred embodiment of the present invention utilizes a hydroxy-(lower alkyl) cellulose as the gelling agent. Typically, hydroxypropylcellulose will be employed in an amount from about 0.1 to about 20 wt %, based on the reservoir fill solution, and preferably from about 0.5 to about 10 wt %. In the example described below, the gelling agent is present in about 2 wt %.

The reservoir or matrix layer also may include diluents, stabilizers, vehicles, biocides, antioxidants, anti-irritants and the like. For example, water is frequently utilized as a diluent in the reservoir type patches. Typically water will be present in the reservoir in an amount not greater than about 50 wt %, based on the reservoir fill solution; preferably, not greater than 40 wt %. Other diluents which will frequently find use in the drug delivery devices described herein include glycerine and propylene glycol.

A pressure-sensitive adhesive layer, is affixed to the membrane opposite to the backing layer. Ideally, the adhesive layer should interact minimally with the drug; it should adhere firmly to the membrane, but removably to the peel strip; it should stick securely to the wearer for extended periods, yet allow the transdermal delivery device to be removed with minimum discomfort; and it should not give rise to undue skin irritation, allergic reactions or other dermatological problems. These properties must be maintained from the time of patch manufacture, throughout storage, and up to and throughout the time of application.

An alternative embodiment of the reservoir patch has a peripheral adhesive, wherein the area of the adhesive layer is not co-extensive with the active releasing area of the patch, but rather forms an annular ring around the active releasing area of the patch. The delivery of the drug thus is not primarily through the adhesive layer of the patch, although some lateral diffusion may occur within the patch, resulting in delivery of active substance through the adhesive at the periphery of the patch. The shape of the peripheral adhesive region will vary with the shape of the patch, but will generally comprise the outer perimeter of the patch, in order that an adequate adhesive seal is maintained between the skin and the patch to prevent the patch from falling off. The percentage of the patch that comprises the peripheral adhesive portion depends on the type of adhesive, the type of backing layer, the length of time the patch will be worn, and the weight and loading of drug in the patch. Such determinations will be apparent to the skilled artisan.

Prior to use, the patches typically are stored in laminate foil pouches, both to prevent contamination and to avoid drug and/or enhancer(s) loss. Such pouches are standard in the industry, and are described in U.S. patent application Ser. No., 08/060,907, the contents of which are expressly incorporated by reference.

The patch may be assembled by any of the techniques known in the art for producing transdermal patches. The patches may be of various shapes, but the round shape is preferred as it contains no corners and thus is less easily detached from the skin.

The dosage units produced may have various sizes. A total surface area in the range of 1 to 200 cm$^2$ is contemplated, with 5–30 cm$^2$ being preferred. Depending on the type of patch, the active drug delivery surface area may be somewhat less than the total surface area, for example, in the peripheral adhesive type reservoir patch. Generally the active drug delivery surface area is in the range of 1–190 cm$^2$, with 5–30 cm$^2$ being preferred.

The percentage by weight of the drug in the solution, hydrogel or matrix may be varied according to the desired loading of the finished patch. The drug content of the finished matrix can vary widely, from about 0.1 to about 70 wt %. Typically, the transdermal patch is applied such that a dose is an amount from 0.1 to 200 mg per day, depending on the therapeutic application.

Generally, dosages for obstructive disorders of the lower urinary tract are between 0.001 and 20 mg/kg/of body weight per day, with preferred dosages being between 0.05 and 1 mg/kg of body weight per day, and most preferred dosages being at least approximately 0.3 mg/kg of body weight per day. For use as an antihypertensive, the dosage of Rec 15/2739 will generally be between 0.01 and 20 mg/kg of body weight per day, with preferred dosages being between 0.1 and 5 mg/kg of body weight per day, and a most preferred dosage being at least approximately 1 mg/kg of body weight per day. For use as a bladder spasmolytic, the general dosage is between 0.10 and 20 mg/kg of body weight per day, with a preferred dosage being 0.02–10 mg/kg of body weight per day, and a most preferred dosage being at least approximately 2 mg/kg of body weight per day. For use in an anxiolytic or antidepressant, the dosage is generally between 0.01–20 mg/kg of body weight per day, with a preferred dosage being between 0.05–5 mg/kg body weight per day, with a most preferred dosage being at least approximately 0.5 mg/kg body weight per day.

The dosage may, however, be more or less depending on factors including therapeutic application, the age of the patient, and the patient's tolerance to the drug, if any. Such dosage changes may be determined by the physician in each case.

The invention is now further illustrated by the following examples which are exemplary but not scope limiting.

EXPERIMENTAL EXAMPLES

EXAMPLE 1

Preparation of 8-{3-[4-(2-methoxyphenyl)-1-piperazinyl] -propylcarbamoyl}-3-methyl-4-oxo-2-phenyl-4H-1-benzopyran A mixture of 6.28 g of 1-(2-methoxyphenyl)piperazine and 5.34 g of 8-(3-chloropropylcarbamoyl)-3-methyl-4-oxo-2 -phenyl-4H-1-benzopyran was heated at 180° C. for 5 hours. After cooling, the dark mass was purified by flash chromatography on silica gel, eluting with dichloromethane/methanol 100:3. The fractions containing the title compound were pooled. The solvents were removed in vacuo and the residue (A) was crystallized from isopropanol, toluene or ethyl acetate to give the anhydrous base (4.6–5.4 mg) melting at 133°–136° C. When the residue (A) is crystallized from a mixture of acetonitrile/water 2:1, a base containing 0.25 molar equivalents of water (m.p.: 104°–106°0 C.) is obtained.

The above-mentioned 8-(3-chloropropylcarbamoyl)-3 -methyl-4-oxo-2-phenyl-4H-1-benzopyran was prepared as follows.

A solution of 1.1 ml of thionyl chloride in 2 ml of chloroform was added to a boiling solution of 3.37 g of 8-(3 -hydroxypropylcarbamoyl)-3-methyl-4-oxo-2-phenyl-4H-1-benzopyran, prepared as described in U.S. Pat. No. 2,921, 070 and in PCT International Publication No. WO93/17007, in 20 ml of chloroform. After stirring for 90 minutes under reflux, the solvent was removed in vacuo and the residue was crystallized from acetonitrile to give 3 g of pure (A), m.p. (188) 193°–194° C., as described in PCT International Publication No. WO93/17007.

EXAMPLE 2

Preparation of 8-{3-[4-(2-methoxyphenyl)-1-piperazinyl]-propylcarbamoyl}- 3-methyl-4-oxo-2-phenyl-4H-1-benzopyran dihydrochloride hemihydrate The residue (A) of Example 1 was dissolved in boiling ethanol. The solution was filtered, acidified with ethanolic hydrogen chloride, and stood overnight at 20°–25° C. The crude product was collected by filtration and crystallized from ethanol to give 5 g of the title compound, m.p. (177) 182°–186° C.

EXAMPLE 3

Preparation of 8-{3-[4-(2-methoxyphenyl)-1-piperazinyl]-propylcarbamoyl}-3-methyl-4-oxo-2-phenyl-4H-1-benzopyran dihydrochloride hemihydrate A solution of 4.48 g of 3-methyl-4-oxo-2-phenyl-4H-1-benzopyran-8-carbonyl chloride in 40 ml of chloroform was added dropwise over a period of 10 minutes at ambient temperature to a solution of 3.74 g of 3-[4-(2-methoxyphenyl)-1-piperazinyl]-propylamine, prepared as described in GB 2,161,807 and 1.97 g of triethylamine in 50 ml of chloroform. After stirring for 2 hours, the solution was washed first with 0.5N hydrochloric acid, secondly with a saturated aqueous sodium bicarbonate solution and finally with water. The chloroform solution was dried on anhydrous sodium sulfate and the solvent was evaporated off in vacuo. The residue (B) was worked up as described in Example 2 to give 6.67 g of the title compound, m.p. (177) 182°–186° C. This represents an alternative route to the product of Example 2.

The following salts were also prepared:

monohydrochloride hydrate, m.p. 151°–154° C., (±)-hemimalonate hydrate, m.p. 110°–112° C.

This example has described the condensation of the amine, 3-[4-(2-methoxyphenyl)-1-piperazinyl]-propylamine, with the carbonyl chloride, 3-methyl-4-oxo-2-phenyl-4H-1-benzopyran-8-carbonyl chloride. It should be noted that the amine can be condensed with the corresponding free acid or the corresponding ethyl ester by heating equimolar amounts thereof with or without a solvent. If a solvent is used, a high boiling point hydrophilic or hydrophobic solvent is appropriate. The amine can also be condensed at room temperature with an equimolar amount of the corresponding free acid in the presence of N,N'-dicyclohexylcarbodiimide and 4-dimethylaminopyridine in a solvent such as dichloromethane, chloroform, tetrahydrofuran or dimethylformamide.

EXAMPLE 4

Preparation of 8-{3-[4-(2-methoxyphenyl)-1-piperazinyl]-propylcarbamoyl}-3-methyl-4-oxo-2-phenyl-4H-1-benzopyran monomethanesulfonate The residue (B) of Example 3 was dissolved in boiling isopropanol and added with 1 molar equivalent of methanesulfonic acid. After cooling to room temperature, filtering and washing the cake with hot acetone, the monomethanesulfonate salt melting at 162°–164° C., was obtained.

EXAMPLE 5

Preparation of 8-{3-[4-(2-methoxyphenyl)-1-piperazinyl]-propylcarbamoyl}-3-methyl-4-oxo-2-phenyl-4H-1-benzopyran monomethanesulfonate monohydrate The monomethanesulfonate salt of Example 4, when recrystallized from water or ethanol/water gives the corresponding monohydrate salt melting in the range of 136°–141° C.

EXAMPLE 6

Preparation of 8-{3-[4-(2-methoxyphenyl)-1-piperazinyl]-propylcarbamoyl}-3-methyl-4-oxo-2-phenyl-4H-1-benzopyran dihydrochloride hemihydrate A mixture of 6.28 g of 1-(2-methoxyphenyl)-piperazine and 5.34 g of 8-(3-chloropropylcarbamoyl)-3-methyl-4-oxo-2-phenyl-4H-1-benzopyran was heated at 180° C. for 5 hours. 8-(3-chloropropylcarbamoyl)-3-methyl-4-oxo-2-phenyl-4H-1-benzopyran was prepared as follows. A solution of 1.1 ml of thionyl chloride in 2 ml of chloroform was added to a boiling solution of 3.37 g of 8-(3-hydroxypropylcarbamoyl)-3-methyl-4-oxo-2-phenyl-4H-1-benzopyran, prepared as described in U.S. Pat. No. 2,921,070 and in PCT International Publication No. WO93/17007, in 20 ml of chloroform. After stirring for 90 minutes under reflux, the solvent was removed in vacuo and the residue was crystallized from acetonitrile to give 3 g of pure title compound, m.p. (188) 193°–194° C., as described in PCT International Publication No. WO93/17007.

After cooling, the dark mass was purified by flash chromatography on silica gel, eluting with dichloromethane:methanol 100:3. The fractions containing the title compound were pooled. The solvents were removed in vacuo and the residue was dissolved in boiling ethanol. The solution was filtered, acidified with ethanolic hydrogen chloride, and stood overnight at 20°–25° C. The crude product was collected by filtration and crystallized from ethanol to give 5 g of the title compound, m.p. (177) 182°–186° C.

EXAMPLE 7

Preparation of 8-{3-[4-(2-methoxyphenyl)-1-piperazinyl]-propylcarbamoyl}-3-methyl-4-oxo-2-phenyl-4H-1-benzopyran dihydrochloride hemihydrate A solution of 4.48 g of 8-chlorocarbonyl-3-methyl-4-oxo-2-phenyl-4H-1-benzopyran in 40 ml of chloroform was added dropwise over a period of 10 minutes at ambient temperature to a solution of 3.74 g of 3-[4-(2-methoxyphenyl)-1-piperazinyl]-propylamine, prepared as described in GB 2161807, and 1.97 g of triethylamine in 50 ml of chloroform. After stirring for 2 hours, the solution was washed first with 0.5N hydrochloric acid, secondly with a saturated aqueous sodium bicarbonate solution and finally with water. The chloroform solution was dried on anhydrous sodium sulfate and the solvent was evaporated off in vacuo. The residue was worked up as described in Example 6 to give 6.67 g of the title compound, m.p. (177) 182°–186° C. This represents an alternative route to the product of Example 6.

The following salts were also prepared:

monohydrochloride hydrate, m.p. 151°–154° C., monomethanesulfonate, m.p. 162°–164° C., and (±)-hemimalate hydrate, m.p. 110°–112° C.

This example has described the condensation of the amine, 3-4[-(2-methoxyphenyl)-1-piperazinyl]-propylamine, with the carbonyl chloride, 3-methyl-4-oxo-2-phenyl-4H-1-benzopyran-8-carbonyl chloride. It should be noted that the amine can be condensed with the corresponding free acid or the corresponding ethyl ester by heating equimolar amounts thereof with or without a solvent. If a solvent is used, a high boiling point hydrophilic or hydrophobic solvent is appropriate. The amine can also be condensed at ambient temperature with an equimolar amount of the corresponding free acid in the presence of N,N'-dicyclohexylcarbodiimide and 4-dimethylaminopyridine in a solvent such as dichloromethane, chloroform, tetrahydrofuran or dimethylformamide.

EXAMPLE 8

In vitro flux of Rec 15/2739 free base through hairless mouse skin

The murine in vitro skin permeation rate of saturated solutions of Rec 15/2739 free base in various enhancer and combination enhancer systems was tested.

The skin permeation rate was measured using a high-throughput screening apparatus as described in U.S. patent application Ser. No. 08/227,964 (Attorney Docket No. 15815-43). Each cell of the apparatus comprises one or more diffusion cells, each with an active area of 0.23 cm$^2$ and a receiving volume of 1 ml. The receiver side of the micro-diffusion cells were filled with 1 ml receptor fluid (10 mM phosphate buffered saline, pH 5.7) by a robot after placing one ball bearing in each cell. Hairless mouse skin with a thickness of between 380 and 650 μm (average thickness 540 μm) was placed and clamped on the lower half of the diffusion cell with the stratum corneum facing the donor compartment. One ball bearing was placed in each donor cell and the donor vehicle solutions were loaded. Typically, four donor cells were tested for each drug/enhancer formulation. The donor cells were capped with rubber stoppers and the assembly was placed in a 32° C. incubator and gently rocked for six hours. After six hours the units were removed from the incubator and disassembled. Excess formulation solution was removed. Each compartment was examined to ensure, undamaged skin and complete coverage of the cells with the skin. Excess formulations were blot dried and the skin was carefully removed from the receiver side of the unit. The receiver solutions were analyzed by HPLC, to determine the cumulative amount of drug permeated across the skin (μg/cm$^2$/hr) in the six hour period.

Cumulative release data are provided in Table 2, which shows the flux of the drug (μg/hr/cm$^2$), for the various tested enhancer combinations.

TABLE 3

Flux of Rec 15/2739 free base Across Hairless Mouse Skin from Single and Combination Enhancer Systems

| Enhancer | Flux (μg/hr/cm$^2$) |
| --- | --- |
| N-methyl pyrrolidone | 5.23 |
| transcutol | 0.77 |
| oleyl alcohol | 0.59 |
| ethanol | 1.90 |
| lexol PG-865 | 0.68 |
| propylene glycol myristate (mirpyl) | 3.88 |
| miglyol | 0.98 |
| propylene glycol | 2.02 |
| cineole | 1.45 |
| isopropyl myristate | 2.47 |
| N-methyl pyrrolidone:Miglyol = 25:75 | 9.13 |
| N-methyl pyrrolidone:Miglyol = 50:50 | 15.53 |
| N-methyl pyrrolidone:Miglyol = 75:25 | 8.72 |
| Propylene glycol:Oleyl alcohol = 25:75 | 24.22 |
| Propylene glycol:Oleyl alcohol = 50:50 | 16.26 |
| Propylene glycol:Oleyl alcohol = 75:25 | 0.95 |
| Transcutol:Oleyl alcohol = 25:75 | 2.57 |

TABLE 3

Flux of Rec 15/2739 free base Across Hairless Mouse Skin from Single and Combination Enhancer Systems

| Enhancer | Flux (μg/hr/cm$^2$) |
| --- | --- |
| Transcutol:Oleyl alcohol = 50:50 | 6.56 |
| Transcutol:Oleyl alcohol = 75:25 | 5.14 |
| N-methyl pyrrolidone:Oleyl alcohol 25:75 | 40.21 |
| N-methyl pyrrolidone:Oleyl alcohol = 50:50 | 59.10 |
| N-methyl pyrrolidone:Oleyl alcohol = 75:25 | 22.71 |
| Transcutol:Isopropyl myristate = 25:75 | 4.20 |
| Transcutol:Isopropyl myristate = 50:50 | 12.53 |
| Transcutol:Isopropyl myristate = 75:25 | 20.09 |
| N-methyl pyrrolidone:Isopropyl myristate = 25:75 | 15.54 |
| N-methyl pyrrolidone:Isopropyl myristate = 50:50 | 24.07 |
| N-methyl pyrrolidone:Isopropyl myristate = 75:25 | 15.07 |

The enhancers tested in Table 3 include single enhancers as well as enhancer combinations. The tested enhancers include solvent type enhancers and plasticizing type enhancers.

Enhancer combinations were prepared to achieve increased flux of Rec 15/2739. Combinations comprising a plasticizer-type enhancer and a solvent-type enhancer were prepared and tested in ratios of 25:75, 50:50, and 75:25, as indicated in Table 2. As can be seen from Table 3, preferred enhancer combinations for delivery of Rec 15/2739 are N-methylpyrrolidone:oleyl alcohol, transcutol:isopropyl myristate, and N-methyl-pyrrolidone:isopropyl myristate. A particularly preferred enhancer combination is a 50:50 ratio of N-methylpyrrolidone and oleyl alcohol.

EXAMPLE 9

In vitro flux of Rec 15/2739 mesylate through hairless mouse skin

The murine in vitro skin permeation rate of the mesylate salt of Rec 15/2739 was measured, using various enhancer systems. The concentration of the drug solution was approximately 100 mg/ml for EtOH:Water:IPM and saturated in all other systems.

The skin permeation rates were measured as described in Example 8, and are shown in Table 4. In Table 4, "IPM" indicates isopropyl myristate, and "PG" indicates propylene glycol.

TABLE 4

Flux of Rec 15/2739 (mesylate) from Various Enhancer Systems

| Enhancer | Flux (μg/hr/cm$^2$) |
| --- | --- |
| EtOH:PG:IPM:Labrafac lipophile | 8.44 |
| EtOH:PG:IPM:Labrafil M2125CS | 17.80 |
| EtOH:PG:IPM:propylene glycol myristate | 25.22 |
| EtOH:PG:IPM:propylene glycol laurate | 19.03 |
| EtOH:PG:IPM:Labrafil M2125CS | 6.08 |
| EtOH:PG:IPM:transcutol | 6.00 |
| EtOH:PG:IPM:labrasol | 9.30 |
| EtOH:PG:IPM:Labrafac Hydro WL 1219 (CCTG) | 19.47 |
| PG:IPM:Labrafil M2125CS | 17.17 |
| PG:IPM:propylene glycol myristate | 25.31 |
| PG:IPM:propylene glycol laurate | 46.29 |
| PG:IPM:Labrafac Hydro WL 1219 | 19.56 |
| PG | 0.45 |
| PG:IPM | 0.59 |
| PG:IPM:Croda chamomile O | 0.47 |
| EtOH:Water:IPM | 8.31 |

EXAMPLE 10

In vitro flux through human skin of Rec 15/2739

The human in vitro skin permeation rate of the mesylate salt and the free base of the drug was measured using two enhancer systems saturated with Rec 15/2739. Glass diffusion cells with an area of 1 cm$^2$ and a receiver volume of approximately 3.3 ml were filled with a degassed phosphate buffer solution with a pH of 5.7. A magnetic stirring bar provided constant mixing. The temperature was kept at 32° C. by a surrounding water jacket. The human skin was placed on the top of the receiver cells and held in place by the donor half which was then clamped down.

500 μl of enhancer/drug solution was then pipetted into the donor cell on the stratum corneum side of the skin and the donor cell covered to avoid evaporation loss. One sample from each cell was collected after 24 hours (23 hours for the mesylate salt). The samples were assayed for the presence of Rec 15/2739 by HPLC. The flux of the drug (in μg/cm$^2$/h) is shown in Table 5. Three cells were tested for each formulation.

TABLE 5

Flux of Rec 15/2739 in Enhancer Solutions Through Human Skin

| Enhancer System (Ratio) | Drug form | Flux of Rec 15/2739 [μg/cm$^2$/h] |
| --- | --- | --- |
| N-methyl-pyrrolidone:Oleyl alcohol (50:50) | Mesylate | 5.32 |
| Propylene glycol:Oleyl alcohol (25:75) | Mesylate | 0.73 |
| N-methyl-pyrrolidone:Oleyl alcohol (50:50) | Free base | 6.79 |
| N-methyl-pyrrolidone: Isopropyl myristate (50:50) | Free base | 3.19 |
| Propylene glycol:Oleyl alcohol (25:75) | Free base | 1.16 |

Thus, the patch size for delivering Rec 15/2739 at a minimum daily dose of, for example 0.75 mg (0.01 mg/kg body weight for an average patient weight of 75 kg) is approximately 5–40 cm$^2$ in these enhancer systems.

EXAMPLE 11

Preparation of adhesive patch

An acrylate adhesive casting solution (Durotak 2516) was prepared containing 7% Rec 15/2739. The casting solution was cast onto a silicone coated release liner (Release Technology 381B) to a thickness of 50–200 μm and dried at room temperature for 20 min. and then at 70° C. for 30 min. A polyester backing (3M 1220) was adhered to the dried adhesive film which was then punched into patches of the desired size.

The drug release from these adhesive patch systems was determined by dissolution test. Glass flow through cells with an area of 1 cm$^2$ and a receiver volume of approximately 3.3 ml were filled with a degassed 10 mM phosphate-buffered saline solution with a pH of 5.7. A magnetic stirring bar provided constant mixing and the temperature was kept at 32° C. by a surrounding water jacket. The patches were attached to the top of the receiver cells and clamped down. The flow of the receiving solution was regulated to 3 ml/h and data points were collected every 3 hours over 24 hours. The samples were assayed for the presence of Rec 15/2739 by HPLC. The results are shown in Table 6.

TABLE 6

| Sampling Interval [hours] | Flux of Rec 15/2739 μg/cm$^2$/h] |
| --- | --- |
| 3 | 29.8 |
| 6 | 21.2 |
| 9 | 14.6 |
| 12 | 10.9 |
| 15 | 8.7 |
| 18 | 6.9 |
| 21 | 5.5 |
| 24 | 6.9 |

EXAMPLE 12

Preparation of adhesive patch with N-methyl-2 pyrrolidone

An acrylate adhesive casting solution (Durotak 2516) is prepared containing 10% Rec 15/2739 and 20% N-methyl-2-pyrrolidone. The casting solution is cast onto a silicone coated release liner (Release Technology 381B) to a thickness of 50–200 μm and dried at room temperature for 20 min. and then at 70° C. for 30 min. A polyester backing (3M 1220) is adhered to the dried adhesive film which is then punched into patches of the desired size.

EXAMPLE 13

Preparation of monolithic foam matrix patch

An acrylate adhesive casting solution (Durotak 2516) is prepared containing 7% Rec 15/2739. Half of the casting solution is cast onto a silicone coated release liner (Release Technology 381B) and the other half onto a backing (3M 1220) to a thickness of 50–200 μm. Both films are dried at room temperature for 20 min. and then at 70° C. for 30 min. Polyurethane foam (Great Western Foam Products) is punched to 20 cm$^2$ disks and adhered to the adhesive film on the release liner with approximately 3 cm distance in-between the disks.

250 μl of a solution containing 42% N-methyl-2-pyrrolidone, 42% oleyl alcohol and 16% Rec 15/2739 (or alternatively 500 μl of a solution containing 17% N-methyl-2-pyrrolidone, 17% oleyl alcohol, 51% isopropyl myristate and 15% Rec 15/2739) are pipetted onto each foam disk. The polyester backing is then adhered with the adhesive side to the foam matrix. Patches of 30 cm² are punched with the foam matrix in the center.

EXAMPLE 14

Preparation of peripheral adhesive monolithic foam matrix patch

A polyester medical tape (3M Corp. or Avery Dennison)—comprising an adhesive layer with a thickness of 1–3 mm in-between a release liner and a backing layer—is affixed to a 20 cm² foil disk after removal of the release liner. The medical tape extends the foil disk area, thereby forming a peripheral adhesive annular element.

A polyethylene foam coated with an adhesive on one side (Coating Sciences RX Series) is punched to an 18 cm² disk and adhered to the center of the foil disk.

250 μl of a solution containing 42% N-methyl-2-pyrrolidone, 42% oleyl alcohol and 16% Rec 15/2739 (or alternatively 500 μl of a solution containing 17% N-methyl-2-pyrrolidone, 17% oleyl alcohol, 51% isopropyl myristate and 15% Rec 15/2739) are pipetted onto each foam disk.

The foam and exposed adhesive area are then covered by a protective release liner (Release Technology 381B).

EXAMPLE 15

Preparation of silicone elastomer matrix patches with peripheral adhesive 45 g of Silastic MDX 4-4210 (Dow Corning Group) is mixed with 5 g of curing agent using a high shear mixer at 2000 rpm. 15 g of this solution is homogenized with 5 g of Rec 15/2739 mesylate solution in Propylene glycol/propylene glycol laurate/Isopropyl myristate (2:1:1) using a high shear mixer. The prepared solution is deaerated in a vacuum (30 mmHg) for one hour and then poured between the uncoated sides of two sheets of polyester membrane (3M Scotchpak Fluoropolymer coated release liner 1022). The units are pulled through the adhesive coating units (Werner Mathis AG) to achieve a uniform thickness film, of between 0.5 and 2.0 mm. The film is cured in a 100° C. oven for 15 minutes. The finished film is cut into disks with desired diameter and the polyester films are removed. These disks are transferred onto an adhesive film (Dow 4201 Silicone adhesive) cast on backing membrane (Scotchpak 1009). Then the release liner (3M 1022) is placed on top and the patches are punched out in a size larger than the silicone elastomer disks to get peripheral adhesive rim. In this patch configuration, silicone elastomer containing drug and enhancer solution is in direct contact with skin and the peripheral rim of adhesive affixes the patch to the skin of the patient.

EXAMPLE 16

Preparation of liquid reservoir transdermal patches

Two Durotak 9852 adhesive solutions were prepared, one containing 30 wt % isopropyl myristate. The adhesive/enhancer solutions were cast on the coated side of a 3M Scotchpak Fluoropolymer coated Release Liner No. 1022 or a Release Technology silicon-coated polyester membrane 381B to a thickness of 75 μm after being dried at room temperature for 30 minutes and then in a 100° C., oven for fifteen minutes. A 3M Cotran microporous polyethylene film membrane No. 9710 and a 3M Scotchpak polyester film laminate No. 1009 backing were laminated onto the adhesive layer. The laminates were heat sealed to obtain 5 cm² active area circles with a narrow neck opening, and were punched out by hand by cutting along the outer edge of the heat seal. These patch shells were weighed before filling. The reservoir of the patch is filled with a drug solution prepared as follows.

Rec 15/2739 fill solutions were prepared using an EtOH:water:IPM (49:49:2) enhancer mixture, with 2% hydroxypropyl cellulose as a gelling agent. The concentration of Rec 15/2739 mesylate was 100 mg/g of vehicle.

The volume of the drug fill solution for each patch was approximately 0.3 ml. The fill solution was loaded with a 1 ml syringe through the opening of the patch, the opening of each patch was heat sealed, and the patches were re-weighed. Patches were stored at room temperature in heat-sealed Barex pouches.

EXAMPLE 17

Hydrogel preparation

To 50 g of water is added 5 g of powdered gelatin and 5 g of dextrin with stirring. The mixture is then heated to boiling. Rec 15/2739 mesylate salt (6.0 g) is dissolved in a minimal amount of water and the resulting aqueous drug solution is added dropwise to the boiling gelatin mixture. A preservative such as benzalkonium chloride (5 mg) may also be added to the boiling mixture. The hot liquid is then poured onto glass plates fitted with teflon dividers; a second glass plate is then placed over the first glass plate containing the hot solution, supported by the teflon dividers. The hot liquid is then allowed to cool to room temperature whereby the solution then sets to form a gel. After setting, the gel is cut into disks, with thicknesses typically ranging from 0.75–1.0 mm. The size of the disks may vary, depending on the desired patch size.

EXAMPLE 18

Preparation of a peripheral adhesive hydrogel transdermal patch

A polyester medical tape (3M Corporation or Avery Dennison), comprising an adhesive layer with a thickness of between 1 and 3 millimeters, sandwiched between a release liner and a backing layer, is affixed to a 5–40 cm² foil disk after removal of the release liner from the medical tape. The area of the foil disk is smaller than that of the medical tape such that the adhesive portion of the medical tape extends outwardly from the foil disk, thereby forming a peripheral adhesive annular element. The disk is then filled with the hydrogel of Example 16, containing drug and optional penetration enhancers. The gel and exposed adhesive surface are then covered by a protective release liner. In an alternate embodiment, it may be desirable to first cover the gel with a microporous membrane such as Cotran 9711.

All publications, patents and patent applications herein are incorporated by reference to the same extent as if each individual publication, patent, or patent application was specifically and individually indicated to be incorporated by reference.

Although the present invention has been described in some detail by way of illustration for the purposes of illustration, description and clarity of understanding, it will be apparent that certain changes and modifications may be practiced within the scope of the claims. The preferred embodiments are not intended to be exhaustive or to limit the invention to the precise form disclosed, and many modifications and variations are possible in light of the above teaching. Such modifications and variations which may be apparent to a person skilled in the art are intended to be within the scope of this invention.

What is claimed is:

1. A transdermal patch for the delivery of Compound IV, having the formula:

Compound IV to the skin of a patient, the patch comprising
 a) a backing layer;
 b) a drug depot selected from the group consisting of a liquid reservoir and a monolithic matrix; said depot comprising compound IV and a permeation enhancer composition; and
 c) means for affixing the patch to the skin of the patient.

2. The transdermal patch of claim 1, wherein the permeation enhancer composition comprises at least one plasticizer enhancer.

3. The transdermal patch of claim 2, wherein at least one plasticizer enhancer is selected from the group consisting of oleyl alcohol, propylene glycol diester decanoic, octanoic acid, miglyol, propylene glyco myristate, cineole, and isopropyl myristate.

4. The transdermal patch of claim 2, wherein the permeation enhancer composition further comprises a solvent enhancer.

5. The transdermal patch of claim 4, wherein the solvent enhancer is selected from the group consisting of ethanol, propylene glycol, transcutol, and N-methyl-pyrrolidone.

6. The transdermal patch of claim 1, wherein the permeation enhancer composition comprises N-methyl-pyrrolidone and oleyl alcohol.

7. The transdermal patch of claim 6, wherein the N-methyl-pyrrolidone and the oleyl alcohol are present in a 1:1 weight ratio.

8. The transdermal patch of claim 1, wherein the means for affixing the patch to the skin of the patient is a peripheral annular adhesive layer.

9. The transdermal patch of claim 1, having an active surface area of less than 30 cm$^2$.

10. The transdermal patch of claim 1, wherein Compound IV is present as the mesylate salt.

11. The transdermal patch of claim 1, wherein Compound IV is present as the free base.

12. A method for administering Compound IV, having the formula:

Compound IV to an individual in a therapeutically effective amount, the method comprising the transdermal administration of Compound IV together with a permeation enhancer composition, sufficient to deliver at least about 0.01 mg of Compound IV per kg of body weight per day to the individual.

13. The method of claim 12 wherein the permeation enhancer composition comprises at least one plasticizer enhancer.

14. The method of claim 13 wherein at least one plasticizer enhancer is selected from the group consisting of oleyl alcohol, propylene glycol diester decanoic, octanoic acid, miglyol, propylene glycol myristate, cineole, and isopropyl myristate.

15. The method of claim 13 wherein the permeation enhancer composition further comprises a solvent enhancer.

16. The method of claim 13 wherein the solvent enhancer is selected from the group consisting of N-methyl-pyrrolidone, transcutol, propylene glycol, and ethanol.

17. The method of claim 12 wherein the permeation enhancer composition comprises N-methyl-pyrrolidone and oleyl alcohol.

18. The method of claim 17 wherein the N-methyl-pyrrolidone and the oleyl alcohol are present in a 1:1 weight ratio.

19. The method of claim 13 wherein the individual is suffering from benign prostatic hyperplasia.

20. A method of treating benign prostatic hyperplasia, the method comprising the transdermal administration of a therapeutically effective amount of compound IV, having the formula:

Compound IV

* * * * *